United States Patent [19]

Engelsberger

[11] Patent Number: 4,547,427
[45] Date of Patent: Oct. 15, 1985

[54] MULTILAYER, STERILIZABLE DEEP-DRAWING FILM

[75] Inventor: Herbert Engelsberger, Viersen, Fed. Rep. of Germany

[73] Assignee: Feldmühle Aktiengesellschaft, Düsseldorf, Fed. Rep. of Germany

[21] Appl. No.: 601,554

[22] Filed: Apr. 18, 1984

[30] Foreign Application Priority Data

Apr. 29, 1983 [DE] Fed. Rep. of Germany ....... 3315582
Apr. 29, 1983 [DE] Fed. Rep. of Germany ....... 3315652

[51] Int. Cl.$^4$ .................. B32B 27/08; B65D 1/34
[52] U.S. Cl. ................................ 428/349; 428/35;
428/520; 53/170; 206/484.2
[58] Field of Search .................. 428/35, 349, 520;
206/484, 484.2, 524.2; 53/170, 173

[56] References Cited

U.S. PATENT DOCUMENTS

| | | | |
|---|---|---|---|
| 3,595,735 | 7/1971 | Tyrrell | 428/220 |
| 3,595,740 | 7/1971 | Gerow | 161/254 |
| 3,697,368 | 10/1972 | Bhuta et al. | 161/227 |
| 3,775,239 | 11/1973 | Snow | 161/250 |
| 3,932,692 | 1/1976 | Hirata et al. | 428/474 |
| 4,079,850 | 3/1978 | Suzuki et al. | 215/1 C |
| 4,329,388 | 5/1982 | Vicik et al. | 428/216 |
| 4,352,702 | 10/1982 | Bornstein | 156/84 |
| 4,382,513 | 5/1983 | Schirmer et al. | 206/484 |

Primary Examiner—John E. Kittle
Assistant Examiner—Thomas C. Saitta
Attorney, Agent, or Firm—Toren, McGeady, Stanger, Goldberg & Kiel

[57] ABSTRACT

A multilayer film and containers made thereof, the film being composed of a four layer composite film produced by flattening upon itself, a two layer coextruded blown tube, the outer layer of said tube being linear polyethylene or high density polyethylene, and the inner layer of said tube being ethylene methacrylic acid copolymer crosslinked with metal ions or an ethylene vinylacetate copolymer, said outer layer and said inner layer of said tube being secured to one another by melt-bonding, whereas the surfaces of said inner layer being secured to one another by a mechanical, detachable heat-bonding, said heat-bonding being achieved by flattening said tube and contacting said surfaces under the influence of heat and pressure.

20 Claims, 8 Drawing Figures

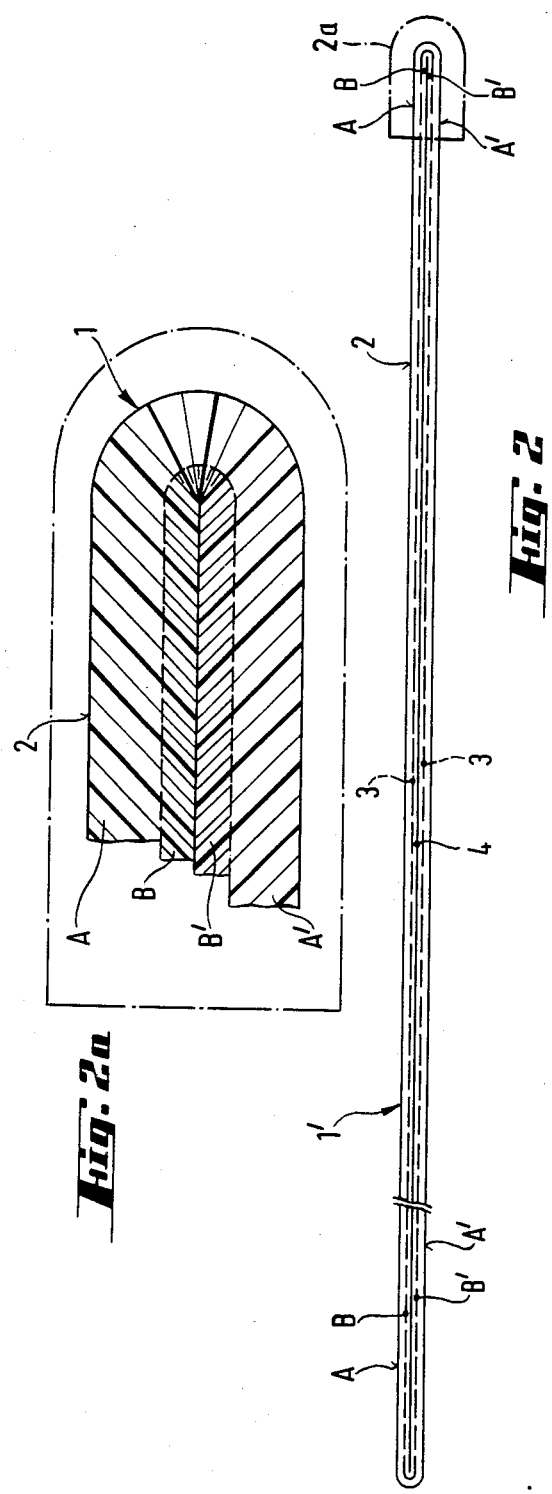

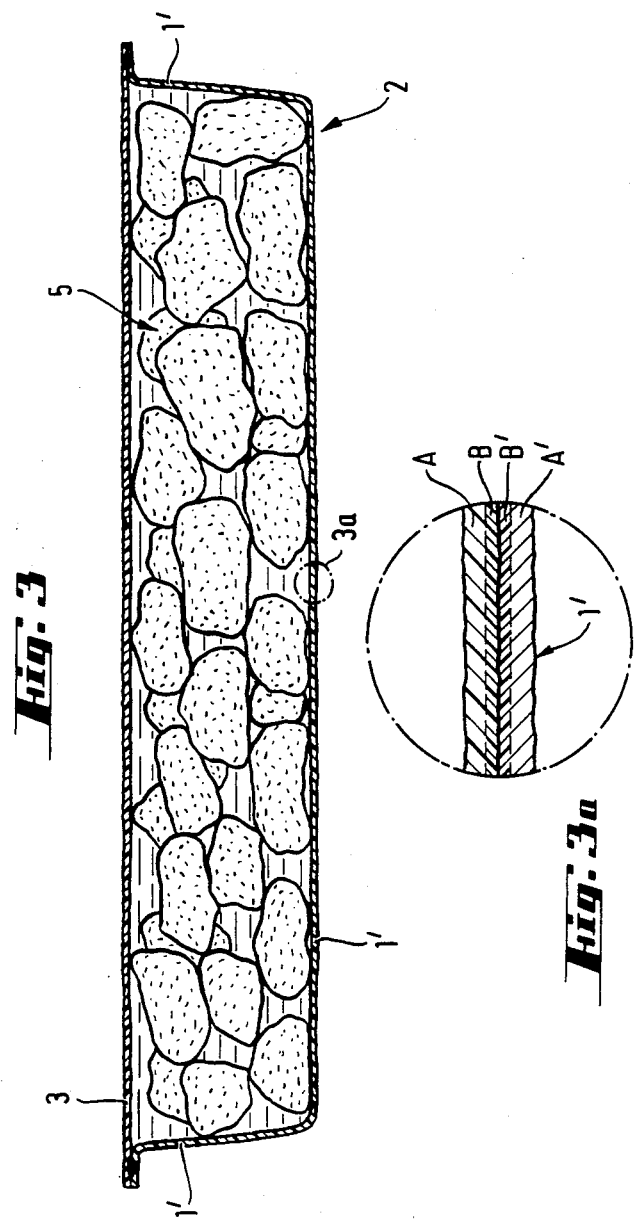

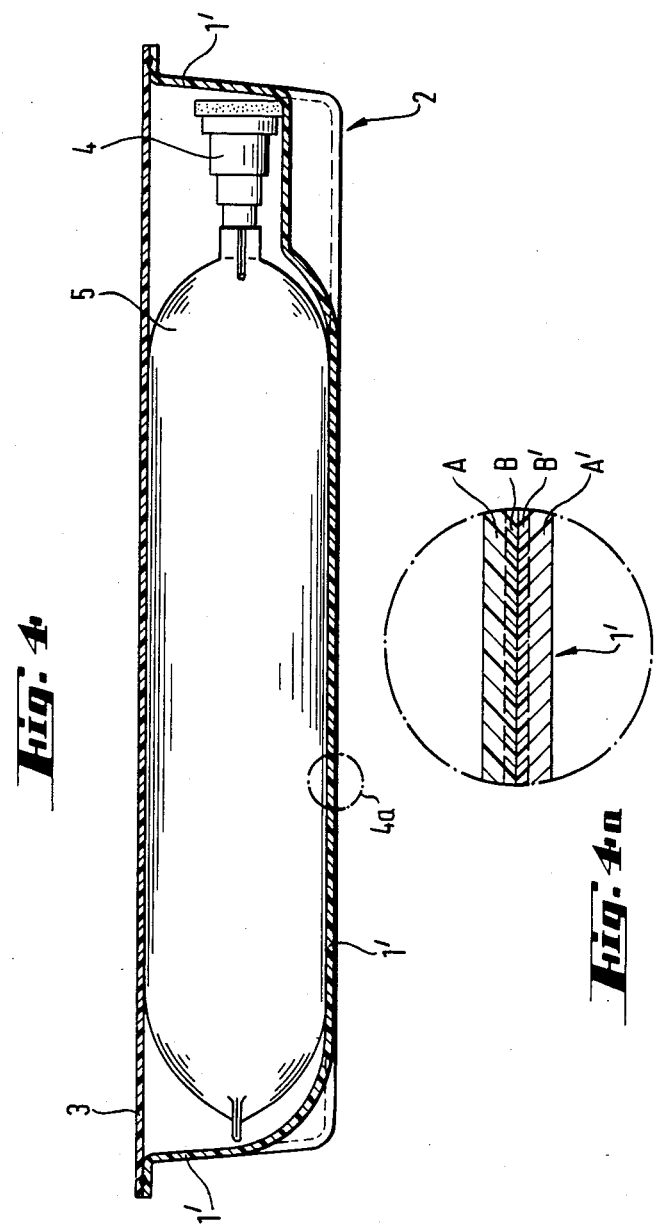

MULTILAYER, STERILIZABLE DEEP-DRAWING FILM

BACKGROUND OF THE INVENTION

1. Field of the Invention

The invention relates to a multilayer, sterilizable deep-drawing film, particularly suitable for the manufacturing of vacuum deep-drawn packagings to hold blood infusion fluids, filled in plastic bags, for manufacturing of low temperature resistant vacuum deep-drawing packagings, or for vacuum deep-drawing packaging of sharp-edged packed goods, and a low temperature resistant vacuum deep-drawing packaging with foods packed therein. Such vacuum deep-drawing packaging is manufactured using the deep-drawing film together with a covering film.

2. Description of the Prior Art

Multilayer, sterilizable deep-drawing films are known for the packaging of blood infusion fluids filled into soft PVC bags with a drain valve, as well as for the manufacturing of low temperature resistant packaging. As support films, deep-drawable composite films are used which consist of unextended polyamide or polyester film, laminated with a film of high density polyethylene (HDPE, low pressure polyethylene) or of unoriented polypropylene (PPUG). While such a film can be excellently fused by means of its polyethylene layer, it has the disadvantage that usually two work steps are necessary to manufacture the two film layers and an additional work step is required for joining the film layers. Also, there is the disadvantage that in order to achieve a satisfactory deep-drawing behavior, one of the two film layers must be made of polyamide or polyester and functions as a supporting film during the deep-drawing process. Thus, when using these relatively expensive raw materials, one can achieve a satisfactory breaking resistance, but must also accept the fact that the packaging, as a whole, cannot be economically manufactured for the particular end use.

Also, other processes for manufacturing of coextruded composite films became known and the use of these processes makes it possible to manufacture a two-layer or multilayer film in one work step. Essentially, composite films are manufactured according to these processes using tubes provided with two or more annularly arranged nozzles. These processes can be divided into the following three groups:

(a) The tubes are used as such for manufacturing of bag packagings;

(b) The tube films are manufactured in the same manner, however, the tube is cut open and the film is used as a flat film.

Both cases always result in films with two layers connected with one another, for instance, when using two ring nozzles. Such films and processes are described in German AS No. 11 36 818 and in German patent No. 12 89 297.

(c) Coextruded composite tubes whose individual layers are combined, for instance, by sealing to a uniform composite film so that a separation of the individual layers is no longer possible (German No. OS 19 66 466 and 21 02 377).

Another disadvantage of the known deep-drawing films which occurs particularly in complicated deep-drawing molds, results from the high stiffness of the polyamide or polyester layers. Due to this stiffness, formation of a deep-drawing film having a consistent shape is not always possible.

Another technical disadvantage of the known, sterilizable deep-drawing film is inadequate breaking resistance during evacuation of the bag, connected with a certain embrittlement during heating. This may result in breaking during sterilizing so that reinfection can occur between the outer and inner packaging, i.e., between the support film and the soft PVC bag, whereby the soft PVC bag is no longer sterile.

SUMMARY OF THE INVENTION

I have discovered a means to overcome these known disadvantages and to develop a sterilizable, highly tough and puncture resistant packaging film which can be manufactured in a single work step, using economical raw materials. Particularly, the invention provides a sterilizable, deep-drawable film with improved breaking strength, which can be used for low temperature resistant vacuum deep-drawing packaging and the vacuum deep-drawing packaging of sharp-edged packed goods, as well as for the manufacturing of deep-drawn packagings to hold blood infusion fluids filled in plastic bags. The invention sees as additional task, the creation of low temperature resistant vacuum deep-drawing packaging for foods.

It is also the task of the invention to make available a sterilizable deep-drawing film (support film) for a vacuum deep-drawing process, which film has an improved deep-drawing behavior and particularly, makes possible a forming with accuracy of shape.

More particularly, my invention provides a multilayer, sterilizable deep-drawing film comprising:

(a) a coextruded composite film (1') with two outer layers (A, A') of linear polyethylene, polypropylene, a copolymer of polypropylene, or of high density polyethylene (low pressure polyethylene, HDPE), said outer layers having the same thickness, and two inner layers (B, B'), of an ethylene vinylacetate copolymer, or ethylene methacrylic acid copolymers crosslinked with metal ions, said inner layers having the same thickness;

(b) the outer layers (A, A') being secured to the inner layers (B, B') by melt bonding, and the inner layers (B, B') being secured by heat bonding.

BRIEF DESCRIPTION OF THE DRAWINGS

FIG. 2 shows the same tube in cross-section, however, in the bonded state.

FIG. 3 shows in section a vacuum deep-drawing packaging according to the invention with a coextruded composite film as support film in accordance with the invention.

FIG. 4 shows a sectional representation of a soft PVC bag with blood infusion fluid which is packed using the coextruded composite film according to the invention as a support film according to the vacuum deep-drawing procedure.

BRIEF DESCRIPTION OF THE PREFERRED EMBODIMENT

Figure 1A:
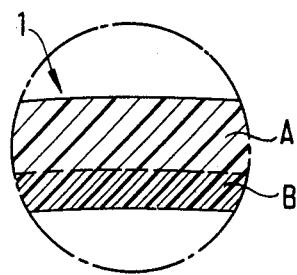
FIG. 1 shows a schematic representation of a two-layer coextruded blown tube in cross-section.
Figure 1:
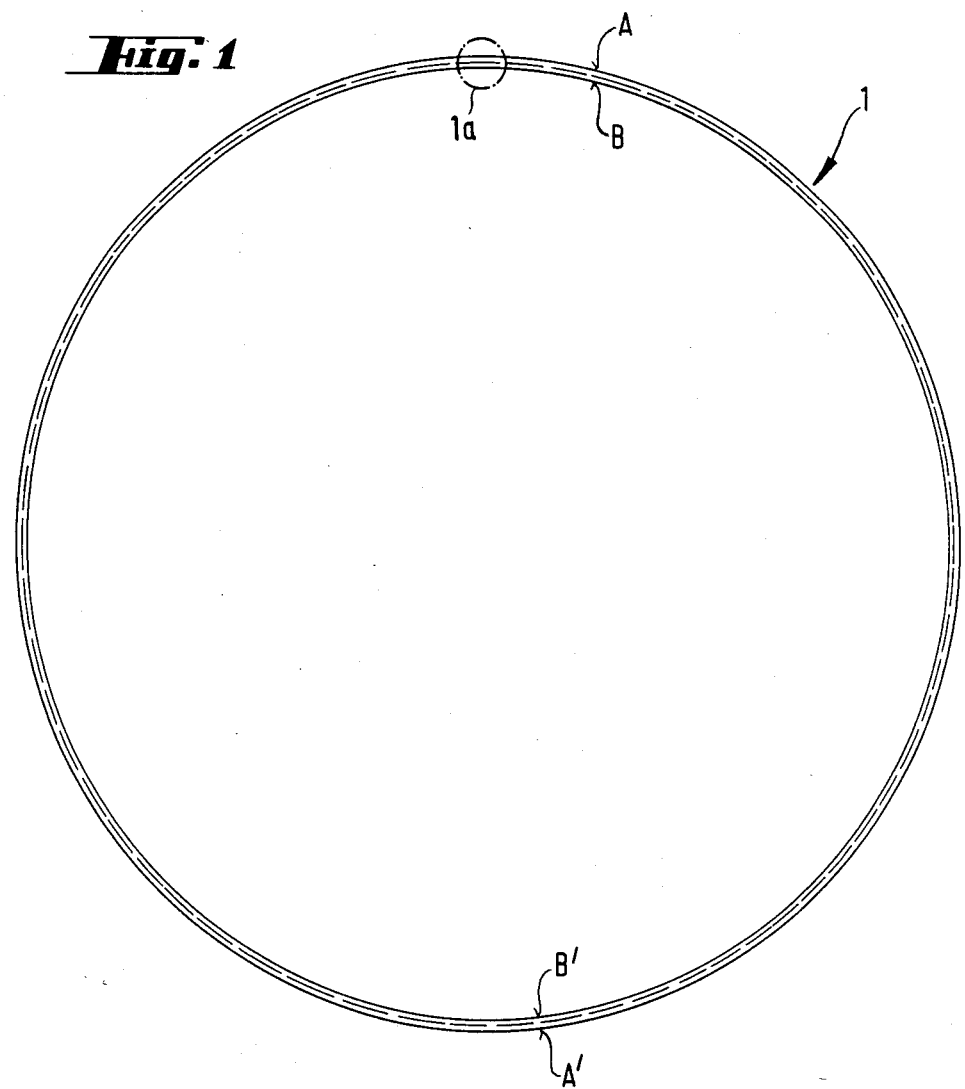

FIG. 1 shows a coextruded blown tube (1) having an outer layer (A, A'), of linear polyethylene, polypropylene, a copolymer of polypropylene or HDPE and an inner layer (B, B') of an ethylene vinylacetate copolymer or ethylene methacrylic acid copolymer crosslinked with metal ions. The circled portion is a detailed view of a coextruded portion of tube (1). As a result of the coextrusion process, layers (A) and (B) are melt bonded to one another, i.e., are extruded side-by-side in molten form and fused together upon cooling.

FIG. 2 shows the coextruded, four-layer composite film (1') which is formed by flattening tube (1), resulting in contacting surfaces (B) and (B'). This can be accomplished by passing the tube through heated opposing squeeze rollers and results in the heat-bonding of surfaces (B) and (B') to one another. As a result, it is possible to mechanically detach layers (B) and (B'). Heat bonding, as used in the present invention, means a connection between the inner layers which still makes possible a mechanical detachment of these two layers. Preferably, the composite adhesion achieved by heat bonding the inner layers is not greater than 100 cN/cm.

The multilayer deep-drawing films of the present invention are suitable for a number of uses. They are particularly suitable for use as (a) packaging of blood infusion fluids and (b) low temperature resistant packaging and vacuum packaging of sharp-edged packed goods. Each of these uses will be discussed separately.

(a) Packaging of Blood Infusion Fluids

Compared to the presently known multilayer deep-drawing films used particularly for packaging of blood infusion fluids filled in plastic bags, the deep-drawing film according to the invention is characterized in that it is made of significantly more economical raw materials than polyamide or polyester, such as, polypropylene, copolymers of polypropylene or high density polyethylene or of ethylene vinylacetate copolymers. Without having a greater thickness than the known deep-drawing films, the multilayer deep-drawing film according to the invention has a surprisingly improved breaking strength. This improvement is due to the very specific construction of the film according to the invention. On the one hand, due to the high elasticity of the inner layers of ethylene vinylacetate copolymers, crack formation does not occur when a vacuum is applied. On the other hand, compared to the outer layers of polypropylene, polypropylene copolymers or of high density polyethylene, they do not harden during cooling following a temperature stress, so that cracking due to embrittlement, if any, occurs in the outer layers, while the undamaged inner layers continue to guarantee a safe enclosure of the packed material. Another reason for the improved breaking strength is that the inner layers are connected with one another only by heat bonding, while they are fused to the outer layers by melt bonding which occurs during the coextrusion of the tube. Since the two inner layers are connected only by heat bonding, they have a degree of mobility with respect to one another, which is particularly advantageous during the deep-drawing process and during the subsequent evacuating and which also contributes to the improvement of the breaking strength.

Particularly, when the outer layers of the film according to the invention consist of polypropylene or a polypropylene copolymer, the film can be completely sterilized at a temperature range between 121° and 135° C., and the film is therefore particularly suitable for packaging of blood infusion fluids filled in plastic bags. Also, when using high density polyethylene (HDPE, low pressure polyethylene) as the outer layer material, the film according to the invention can be used for this same purpose and can be sterilized at temperatures at the lower boundary value of 121° C.

To achieve an optimum deep-drawing behavior, it is understood that the four-layer film obtained by coextrusion according to the invention is left in the unoriented state.

A special advantage of the deep-drawing film according to the invention lies in its excellent deformability, so that it can be used for the manufacturing of complicated deep-drawing molds. In the packaging of plastic bags containing blood infusion fluids and having a drain valve, the film allows an exact forming of the deep-drawing mold, which corresponds to the plastic bag and the drain valve.

A preferred embodiment of the invention for this use provides outer layers of a polypropylene copolymer with a proportion of 1 to 5 mole %, and especially preferred, 2 to 4 mole % of ethylene. These plastics have a melt index of 0.3 to 15, preferably of 1 to 10 g/10 minutes at 230° C./2.16 kg load, corresponding to ISO/R 133, procedure 12.

These propylene-ethylene copolymers are identified as so-called random copolymers. Compared to polypropylene homopolymer, they offer the advantage that they can be sealed at low temperatures and have a wider sealing temperature range. In addition, they have a higher strength at low temperature.

To achieve a high composite strength by means of melt bonding between the outer and inner layers of the coextruded composite film according to the invention, inner layers of an ethylene vinylacetate copolymers are preferred which contain 10 to 35 weight percent vinylacetate, and particularly preferred are 20 to 28 weight percent vinyl-acetate. The melt index of these plastics lies at 0.5 to 8, preferably at 1.5 to 4 g/10 minutes at 190° C. and 2.16 kg load, according to DIN 53735. These inner layers offer the additional advantage of heat bonding very strongly with one another so that during the heat bonding process, air inclusions are prevented. Consequently, during the heating necessary for sterilization, visible bubbles which would interfere with the optical impression, do not form. During heating, for instance, during sterilizing of the packed material, fusion of the inner layers may occur, depending on the temperature applied. However, the excellent breaking strength of the coextruded composite film is not impaired by this because any melt bonding of the inner layers which may occur, takes place only after the critical process steps of deep-drawing and evacuating.

An additional, especially preferred embodiment comprises outer layers of a copolymer of propylene with an ethylene portion of 2 to 4 mole percent and inner layers of a copolymer of ethylene vinylacetate with a vinyl acetate portion of 20 to 28 weight percent. Such a four-layer, coextruded composite foil exhibits a definite flexible deep-drawing behavior at a temperature of 125° C., and the deep-drawing mold formed from this foil is particularly tough and break resistant.

Especially preferred embodiments of the coextruded composite film provide a total thickness which lies between 100 and 330 μm wherein the outer layer has a thickness of not more than 4/5 and not less than ½ and the inner layers a thickness of not more than ½ and not less than 1/5. The plastics suggested for manufacturing of the outer layers according to the present invention fulfill the requirement of a good fusibility with the covering film of a deep-drawing packaging.

In connection with this type of use and referring to FIG. 1, preferably, the outer layer (A) consists of a copolymer of propylene with 2.7 mole % ethylene proportion and a melt index of 3 g/10 minutes. The inner layer (B) consists of an ethylene-vinylacetate copolymer with 25 weight percent vinylacetate proportion. Layers (A) and (B) are combined by melt bonding.

FIG. 2 shows the coextruded, four-layer composite film (1') which is formed by flattening and heat bonding the inner layer (B) of the blown tube (1) shown in FIG. 1. For this use, preferably, the composite film has outer layers (A, A') formed of polypropylene copolymer and inner layers (B, B') formed of ethylene vinylacetate copolymer. The outer layers (A, A') have a thickness of 70 μmm, and the inner layers (B, B') have a thickness of 35 μmm which results in a total thickness of 210 μmm.

FIG. 4 shows a deep-drawing packaging (2) in which a bag (5), made of soft PVC and containing blood infusion fluid with a drain valve (4) is packed. The covering film (3) is a two-layer composite film, consisting of a 15 μmm thick, biaxially oriented polyamide film, laminated with a 50 μm thick unoriented polypropylene film. The support film is made of the coextruded composite film (1') (heat bonded tube) according to the invention described in FIGS. 1 and 2.

(b) Low-Temperature Resistant Packaging and Vacuum Packaging of Sharp-Edged Packed Good Compared to the presently known, multilayer deep-drawing films for low temperature resistant vacuum deep-drawing packagings or for the vacuum packaging of sharp-edged packed goods, the deep-drawing film according to the invention, is characterized in that it consists of raw materials which are much more economical compared to polyamide, such as, linear polyethylene or high density polyethylene, or of ethylene vinylacetate copolymers or of ethylene methacrylic acid copolymers crosslinked with metal ions. Although the deep-drawing film according to the invention does not have a greater thickness than the known deep-drawing films, it has, surprisingly, an equally good tenacity and puncture resistance. The excellent strength of the deep-drawing film according to the invention is explained for one, by the high mechanical shock resistance of the raw material groups used for manufacturing of the outer and inner layers, which can reach in the individual case, for instance, in the linear low density polyethylenes (LLDPE) which belong to the linear polyethylenes, peak values of up to 175 cN. In the case of the ethylene methacrylic acid copolymers, crosslinked with metal ions, which are also suitable for manufacturing the inner layers, the mechanical shock resistance is still significantly higher and may be up to approximately 450 cN.

All data on the mechanical shock resistance in the present application are based on the measurements according ASTM D-1709-62 at a drop height of 650 mm and a film thickness of 25 μm.

It is believed that the high puncture resistance exhibited by the film of the invention results from the outer layers of a coextruded tube flat being connected with the inner layers during the extrusion by means of melt bonding, but the inner layers are only combined by heat bonding. Preferably, the composite adhesion achieved by heat bonding the inner layers is not greater than 100 cN/cm. Such heat bonding is achieved advantageously using heat and pressure by means of a pair of squeeze rollers.

Contrary to the films known from German OS No. 21 02 377, in which the separability of the individual layers in the completed composite film is explicitly excluded, in the deep-drawing film according to the invention, due to the inner layers which are merely combined by heat bonding, a tear-stop results which is explained as follows:

When a puncture stress acts on the deep-drawing film according to the invention, for instance, by a sharp-edged bone which presses from the interior of a deep-drawing packaging onto the deep-drawing film, at the stressed area a tear of the two film layers, i.e., outer layer/inner layer combined by means of melt bonding, may occur. This tear is directly adjacent to the stressed area. However, for the destruction of the two additional layers of the deep-drawing film according to the invention, i.e., inner layer/outer layer, the sharp-edged bone would have to overcome again the tear resistance of these two layers at the heat bonded area in order to be able to also tear these two layers. But since the tear resistance in all flat structures is higher than the tear-off resistance, the puncture force of the bone encounters a resistance which protects the deep-drawing film from further destruction and guarantees the tightness of the packaging.

Linear polyethylenes, in the sense of the present invention, are understood to be those which are prepared by copolymerization of ethylene with minor proportions of α-olefin comonomers ($C_3$ to $C_{12}$). LLDPE (linear low density polyethylene) with a density of 0.918 to 0.945, preferably 0.922 to 0.930, is particularly suitable. The melt index of this polyethylene is about 0.2 to 4.0, preferably about 0.8 to 1.5. This group of materials is particularly suited for the purpose of the present invention because, due to the high tenacity of LLDPE in the multilayer deep-drawing film according to the invention, a particularly high puncture resistance can be achieved. For the same reason, also HDPE with a density of at least about 0.935, and preferably about 0.950 to 0.965, and a melt index of from about 0.2 to 4.0, is an excellently suitable material for the purpose of the invention.

The copolymers of ethylene with vinylacetate, and the ethylene methacrylic acid copolymers crosslinked with metal ions, which are also identified as ionomeric resins and are sold by Dupont under the tradename "Surlyn", can be used according to the invention for manufacturing of the inner layers. They heat bond well with one another, but still guarantee a certain mobility during deep-drawing, i.e., the two outer layers which are always combined with the inner layers by melt bonding, are still mobile to a minor extent with respect to one another at the area, at which the two inner layers are heat bonded. Thus, during the deep-drawing process, the outer layer of, for instance, LDPE, which forms the interior of the deep-drawing trough and an inner layer of, for instance, ethylene vinylacetate copolymer, secured to one another by melt bonding, are not automatically subject to an equally strong expansion during construction of the deep-drawing trough as the other outer layer which consists of LDPE and is combined with an inner layer of ethylene vinylacetate copolymer.

The ethylene methacrylic acid copolymers crosslinked with metal ions, of which particularly those crosslinked with sodium or zinc ions are preferred, have a particularly high mechanical shock resistance and also exhibit excellent heat bonding behavior. Even so, their use remains reserved for a few special purposes, for instance, when an extremely high puncture resistance is required or when a particularly low thickness of the multilayer deep-drawing film is desired. Consequently, the inner layers must be manufactured with a relatively small thickness from a material which has a particularly high mechanical shock resistance. However, for most purposes of the invention, the copolymers of ethylene vinylacetate have proven to be excellently suitable and they are therefore especially preferred.

In a particularly preferred embodiment, the deep-drawing film according to the invention provides inner layers of an ethylene vinylacetate copolymer which contains from about 8 to 35 weight percent, preferably 15 to 28 weight percent, vinylacetate. The use of these ethylene vinylacetate copolymers with a melt index of 0.5 to 8, preferably, 1.5 to 4 g/10 minutes at 190° C. and 2.16 kg load according to DIN 53735, guarantees a particularly good melt bonding with the outer layers of linear polyethylene or high density polyethylene during the coextrusion and imparts an extremely high elasticity and puncture resistance to the multilayer deep-drawing film.

Another preferred embodiment of the present invention provides that the coextruded composite film has a total thickness between about 100 and 300 μm, while the outer layers have a thickness of not more than 4/5 and not less than ½ and the inner layers a thickness of not more ½ and not less than 1/5 of the total thickness. For use in low temperature resistant deep-drawing packagings, a total thickness of the film according to the invention of about 190 to 250 μm has proven to be particularly suitable.

In connection with this type of use, and referring to FIG. 1, the outer layers (A, A') consist of LLDPE having a mechanical shock resistance of 170 cN, a melt index of 1.0 and a density of 0.930, while the inner layers (B, B') are made of an ethylene vinylactate copolymer with 25 weight percent vinylacetate portion and a melt index of 3. The layers (A) and (B) are combined with one another by melt bonding.

In FIG. 2, outer layers (A, A') are made of LLDPE and the inner layers (B, B') are made of ethylene vinylacetate copolymer. The outer layers (A, A') have a thickness of 60 μm, the inner layers (B, B') are 30 μm thick which results in a total thickness of 180 μm.

In FIG. 3, a low temperature resistant vacuum deep-drawing packaging (2) is shown in which stew (5) is packed. The cover film (3) is a two-layer composite film, known per se, consisting of a 30 μm thick, unoriented polyamide film, laminated with a 75 μm thick unoriented polyethylene film. The support film (2) consists of the coextruded composite film (1') according to the invention as described regarding FIGS. 1 and 2.

EXAMPLE

The following example describes a multilayer deep-drawing film according to the invention as is used in the deep-drawing packaging of a sharp edged metal powder with grains of approximately 1 to 3 mm diameter which is sold as a welding aid under the tradename "Thermit" by Goldschmidt AG, Essen.

The outer layers (A, A') of such a multilayer deep drawing film consist of LLDPE with a density of approximately 0.92 and a melt index of 1. The thickness of each outer layer is 80 μm.

The outer layers (A, A') are combined by melt bonding with the inner layers (B, B'), which consist of a copolymer of ethylene with 8 weight percent vinylacetate portion and a melt index of 1.5, while the inner layers (B, B') are heat bonded. The inner layers have a thickness of 40 μm each which results in a total thickness of 240 μm for the multilayer deep-drawing film.

As a test of the packaging showed, the described multilayer deep-drawing film has an excellent puncture resistance against the sharp edged metal powder, even at temperatures which lie below the freezing point.

I claim:

1. A multilayer deep-drawing film for use in low temperature resistant vacuum deep-drawing packaging or vacuum deep-drawing packaging of sharp edged packed goods, comprising a four layer composite film produced by flattening upon itself, a two layer coextruded blown tube, the outer layer of said tube being linear polyethylene or high density polyethylene, and the inner layer of said tube being ethylene methacrylic acid copolymer crosslinked with metal ions or an ethylene vinylacetate copolymer, said outer layer and said inner layer of said tube being secured to one another by melt-bonding, whereas the surfaces of said inner layer are coextensively secured to one another by a mechanical, detachable heat-bonding, said heat-bonding being achieved by flattening said tube and contacting said surfaces under the influence of heat and pressure.

2. The multilayer deep-drawing film of claim 1 wherein said inner layers (B, B') consist of an ethylene vinylacetate copolymer which contains 8 to 35 weight percent vinylacetate.

3. The multilayer deep-drawing film of claim 2 wherein the amount of vinylacetate is from 20 to 28 weight percent.

4. The multilayer deep-drawing film of claim 1 or 2, wherein the coextruded composite film as flattened has a total thickness between 100 and 300 μm, the flattened outer layer has a total thickness of not more than 4/5 and not less than ½ and the flattened inner layer has a total thickness of not more than ½ and not less than 1/5 of the total thickness of the tube.

5. A container for foods comprising a low temperature resistant vacuum deep-drawing support film formed in the shape of a chamber, having an opening and a covering film forming a closure for the opening, said support film of said vacuum deep-drawing packaging comprising a four layer composite film produced by flattening upon itself, a two layer coextruded blown tube, the outer layer of said tube being linear polyethylene or high density polyethylene, and the inner layer of said tube being ethylene methacrylic acid copolymer crosslinked with metal ions or an ethylene vinylacetate copolymer, said outer layer and said inner layer of said tube being secured to one another by melt-bonding, whereas the surfaces of said inner layer are coextensively secured to one another by a mechanical, detachable heat-bonding, said heat-bonding being achieved by flattening said tube and contacting said surfaces under the influence of heat and pressure.

6. The container of claim 5 wherein said inner layer consist of an ethylene vinylacetate copolymer which contains 8 to 35 weight percent vinylacetate.

7. The container of claim 6 wherein the amount of vinylacetate is from 20 to 28 weight percent.

8. The container of claim 5 or 6 wherein the coextruded composite film as flattened has a total thickness between 100 and 300 μm, the flattened outer layer has a total thickness of not more than 4/5 and not less than ½ and the flattened inner layer has a total thickness of not more than ½ and not less than 1/5 of the total thickness of the tube.

9. A multilayer, sterilizable deep-drawing film for the manufacturing of vacuum deep-drawn packagings to hold blood infusion fluids filled in plastic bags, comprising a four layer composite film produced by flattening upon itself, a two layer coextruded blown tube, the outer layer of said tube being linear polyethylene or high density polyethylene, and the inner layer of said tube being ethylene methacrylic acid copolymer crosslinked with metal ions or an ethylene vinylacetate copolymer, said outer layer and said inner layer of said tube being secured to one another by melt-bonding, whereas the surfaces of said inner layer are coextensively secured to one another by a mechanical, detachable heat-bonding, said heat-bonding being achieved by flattening said tube and contacting said surfaces under the influence of heat and pressure.

10. The film of claim 9, wherein said outer layer consist of a polypropylene copolymer with a proportion of 1 to 5 mole percent ethylene.

11. The film of claim 10 wherein the amount of ethylene is from 2 to 4 mole percent.

12. The film of claim 9 or 10 wherein the inner layer consist of an ethylene vinylacetate copolymer which contains 10 to 35 weight percent vinylacetate.

13. The film of claim 12 wherein the amount of vinylacetate is from 20 to 28 weight percent.

14. The film of claim 9 or 10 wherein the coextruded composite film as flattened has a total thickness between 60 and 500 μm, the flattened outer layer has a total thickness of not more than 4/5 and not less than ½ and the flattened inner layer has a total thickness of not more than ½ and not less than 1/5 of the total thickness of the tube.

15. A container for a plastic bag which contains blood infusion fluid comprising a sterilizable vacuum deep-drawing support film formed in the shape of a chamber for receiving said bag, said chamber having an opening and a covering foil forming a closure for the opening, said support film of said vacuum deep-drawing packaging comprising a four layer composite film produced by flattening upon itself, a two layer coextruded blown tube, the outer layer of said tube being linear polyethylene or high density polyethylene, and the inner layer of said tube being ethylene methacrylic acid copolymer crosslinked with metal ions or an ethylene vinylacetate copolymer, said outer layer and said inner layer of said tube being secured to one another by melt-bonding, whereas the surfaces of said inner layer are coextensively secured to one another by a mechanical, detachable heat-bonding, said heat-bonding being achieved by flattening said tube and contacting said surfaces under the influence of heat and pressure.

16. The container of claim 15 wherein said outer layer consist of a polypropylene copolymer with a proportion of 1 to 5 mole percent ethylene.

17. The container of claim 16 wherein the amount of ethylene is from 2 to 4 mole percent.

18. The container of claim 15 or 16 wherein the inner layer consist of an ethylene vinylacetate copolymer which contains 10 to 35 percent vinylacetate.

19. The container of claim 18 wherein the amount of vinylacetate is from 20 to 28 weight percent.

20. The container of claim 15 or 16 wherein the coextruded composite film as flattened has a total thickness between 60 and 500 μm, the flattened outer layer has a total thickness of not more than 4.5 and not less than ½ and the flattened inner layer has a total thickness of not more than ½ and not less than 1/5 of the total thickness of the tube.

* * * * *